United States Patent [19]

Ratner

[11] Patent Number: 5,154,179

[45] Date of Patent: * Oct. 13, 1992

[54] DEVICE CONSTRUCTION AND METHOD FACILITATING MAGNETIC RESONANCE IMAGING OF FOREIGN OBJECTS IN A BODY

[75] Inventor: Adam V. Ratner, Foster City, Calif.

[73] Assignee: Medical Magnetics, Inc., Los Altos Hills, Calif.

[*] Notice: The portion of the term of this patent subsequent to Feb. 5, 2008 has been disclaimed.

[21] Appl. No.: 643,618

[22] Filed: Jan. 22, 1991

Related U.S. Application Data

[63] Continuation of Ser. No. 345,892, Apr. 28, 1989, Pat. No. 4,989,608, which is a continuation-in-part of Ser. No. 79,268, Jul. 2, 1987, abandoned.

[51] Int. Cl.$^5$ ............................................. A61B 5/055
[52] U.S. Cl. .................................. 128/653.4; 128/654; 128/656; 128/658; 604/264
[58] Field of Search .... 128/653 A, 653 CA, 658-659, 128/653 R, 654-656, 653.2, 653.4, 653.1; 604/264, 280; 606/28; 600/12

[56] References Cited

U.S. PATENT DOCUMENTS

| | | | |
|---|---|---|---|
| 4,027,659 | 6/1977 | Slingluff | 128/658 |
| 4,431,005 | 2/1984 | McCormick | 128/656 |
| 4,571,240 | 2/1986 | Samson et al. | 128/658 |
| 4,572,198 | 2/1986 | Codrington | 128/653 A |
| 4,577,637 | 3/1986 | Mueller, Jr. | 128/658 |
| 4,608,986 | 9/1986 | Beranek et al. | 128/786 |
| 4,709,703 | 12/1987 | Lazarow et al. | 128/654 |
| 4,719,098 | 1/1988 | Wienmann et al. | 128/653.1 |
| 4,834,964 | 5/1989 | Rosen | 128/653.1 |
| 4,859,450 | 8/1989 | Knaw et al. | 424/9 |
| 4,863,715 | 9/1989 | Jacobsen et al. | 424/9 |
| 4,909,257 | 3/1990 | Englestad et al. | 424/9 |
| 4,951,673 | 8/1990 | Long | 128/653 CA |
| 4,985,233 | 1/1991 | Klaveness et al. | 128/653 A |
| 4,989,608 | 2/1991 | Ratner | 128/653 A |

*Primary Examiner*—Kyle L. Howell
*Assistant Examiner*—Krista M. Pfaffle
*Attorney, Agent, or Firm*—Millen, White & Zelano

[57] ABSTRACT

Device construction facilitating the visibility of a device when inserted into a body being subjected to magnetic resonance imaging having a member adapted to be inserted into the body. The member carries material exhibiting a characteristic under magnetic resonance imaging which differs substantially from that of the body so that the visibility of the member under magnetic resonance imaging is substantially enhanced.

Method for imaging foreign objects in a body having tissue by the use of magnetic resonance imaging and x-ray imaging. The method comprises the steps of causing the foreign object to carry at least one material causing the foreign object to exhibit a characteristic under magnetic resonance imaging which differs from the characteristic of the tissue of the body to enhance the visibility of the foreign object when positioned in the body and also to exhibit a characteristic under x-ray imaging. The foreign object is inserted into the body. The body is then subjected to magnetic and radiofrequency fields to create magnetic resonance in the body and in the foreign object. A magnetic resonance image of the foreign object in the body is then displayed. The body is also subjected to x-rays. An x-ray image of the foreign object in the body is then displayed.

14 Claims, 3 Drawing Sheets

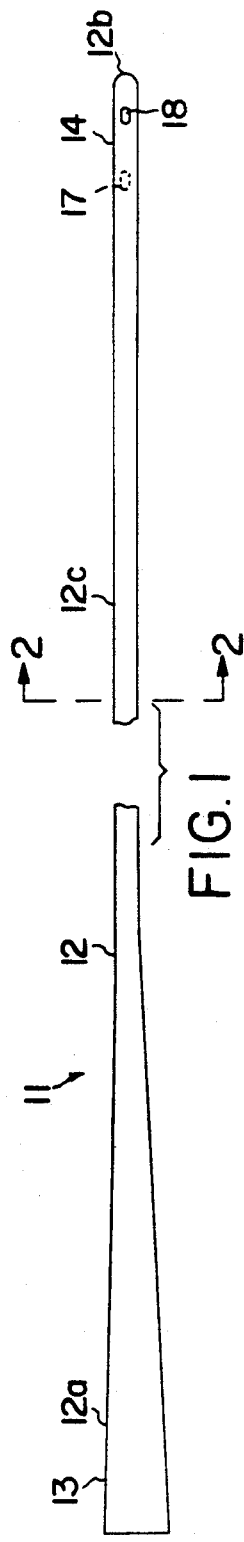
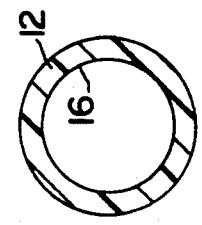
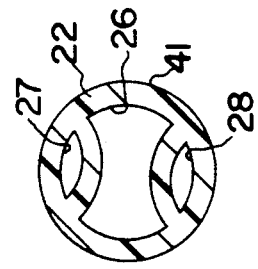
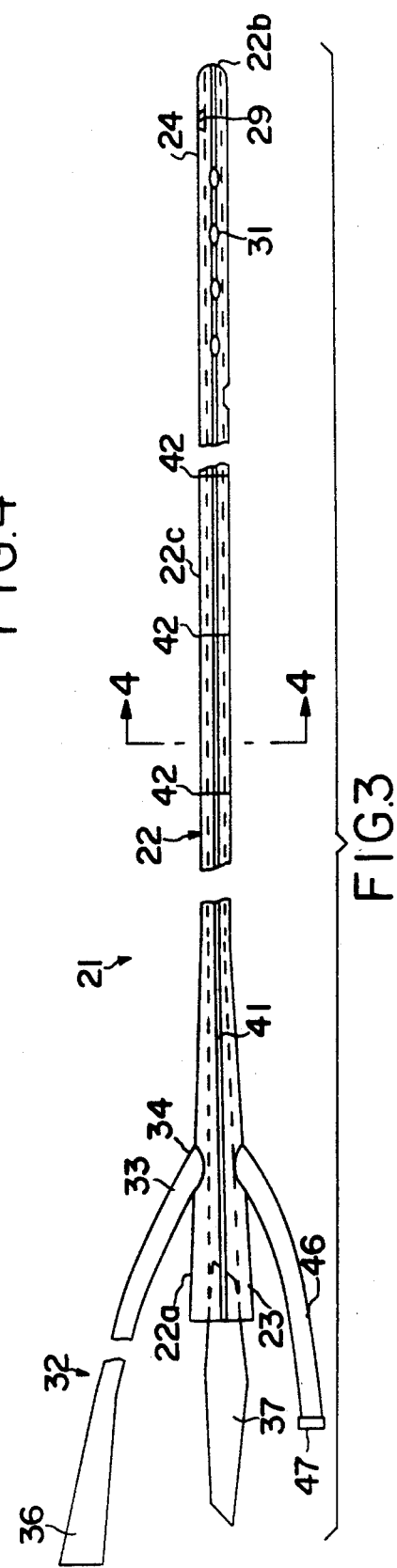

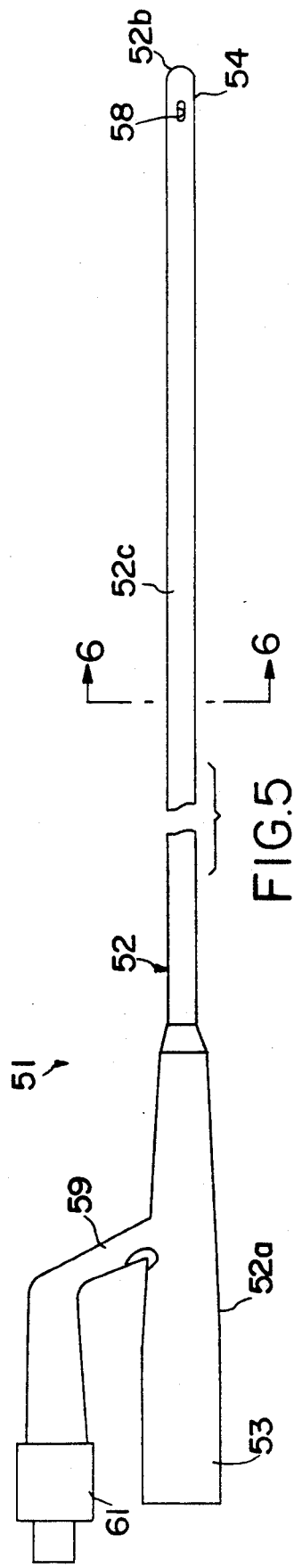
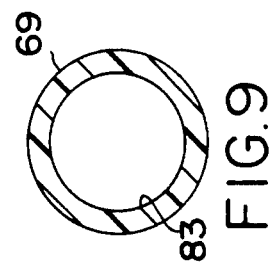
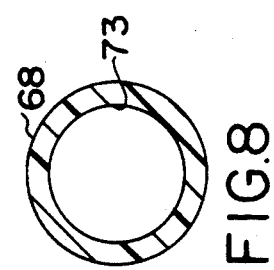
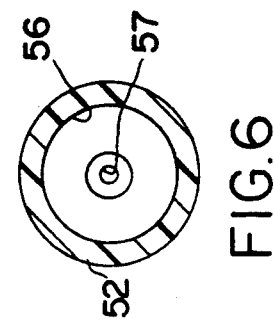

DEVICE CONSTRUCTION AND METHOD FACILITATING MAGNETIC RESONANCE IMAGING OF FOREIGN OBJECTS IN A BODY

This application is a continuation of application Ser. No. 07/345,892, filed Apr. 28, 1989, now U.S. Pat. No. 4,989,608 which is a continuation-in-part application of application Ser. No. 07/079,268 filed on Jul. 2, 1987, now abandoned.

This invention relates to a device construction and method for facilitating magnetic resonance imaging of foreign objects in a body.

BACKGROUND OF THE INVENTION

Proton magnetic resonance imaging (MRI) has gained an increasing role in the diagnosis and assessment of human pathology. In patients undergoing MRI, there are numerous catheters, tubes, and other devices which are poorly seen, if they are visible at all, on the MR image. The location and course of these implanted devices is usually of great clinical importance to assure their proper function and avoid complications that malposition can cause.

Virtually all implantable catheters and similar devices are manufactured so that their locations can be determined using conventional X-ray or X-ray computed tomographic (CT) images. The techniques used to make these catheters visible on such X-ray images are not capable of rendering these catheters reliably detectable on MRI scans.

By stimulating protons in the body's molecules using the principles of nuclear magnetic resonance, images of the human body can be produced rapidly and non-invasively. Magnetic resonance images are produced from complex interactions of magnetic and radiofrequency fields without need of harmful ionizing radiation. The signal intensity or brightness of organs in a human body in a magnetic resonance image is dependent on numerous factors including intrinsic biophysical characteristics of the tissue, the radiofrequency pulse sequence or imaging technique employed to make the image, and properties of the ambient magnetic field. Tissue characteristics in the human body which impact on MRI signal intensity of a structure include proton density (number of protons per volume) and the biophysical relaxation times T1 and T2. Both normal and diseased organs have characteristic values of proton density, T1, and T2 at any given magnetic field strength. Images may be made to highlight or map tissue proton density, T1 and T2 by using different radiofrequency pulse sequences. Pulse sequences may provide different degrees of weighting of each of these characteristics for a variety of clinical purposes. Other pulse sequences have been designed to map organ motion and blood flow and are much less sensitive to differences in T1 and T2 values in the body tissues. In any given MR image there are usually a wide grey-scale range of signal intensities, from very dark to very bright. The grey-scale intensity of a given anatomic region acquired with different pulse sequences and acquisition techniques can vary substantially. For optimum conspicuity, a catheter must be manufactured so that it can be seen in dark, bright, and intermediate signal intensity anatomic regions on all types of MRI scans.

Image signal intensity is also affected by the magnetic environment. The overall strength of the imaging magnet will affect the tissue relaxation times and hence signal intensity. The strength and direction of the magnetic field gradients used in each pulse sequence to provide spatial and contrast information also significantly impact signal intensity and image appearance.

Local magnetic field non-uniformities can cause warping or even complete elimination of detectable signal. Small non-ferromagnetic metal particles can cause local image voids to occur. Ferromagnetic particles in general can cause magnetic field artifacts (MRI signal voids, with adjacent very bright signal bands, hereinafter called "imaging artifacts") which are considerably larger than the size of the particle.

Commonly used implanted medical devices are often difficult to see on MRI scans because they fail to produce sufficient contrast with respect to the surrounding body tissue or structures and/or are too small to be readily detected. Specifically this is true for foreign objects such as catheters which are introduced into the body. U.S. Pat. No. 4,572,198 so appreciated the problem and stated that if the structural portions of the catheter are simply more hydrogenous than the tissue surrounding, the catheter is detectable but a limit is placed on the available contrast. Because of the electronic noise that they introduce to the imaging apparatus, additional functional elements such as electrode wires and the like employed in U.S. Pat. No. 4,572,198 significantly degrade the magnetic resonance image often to the point of complete image obliteration. If it is usable at all, the resulting image would be clinically less diagnostic and would make accurate localization of the implanted catheter difficult if not impossible. This appears at best to be a difficult and tenuous solution to the problem. There is therefore a need for a new and improved device construction and a method so that the device inserted into the body can be more conspicuous from within different body structures yet not degrade the overall magnetic resonance image quality.

There is no intrinsic incompatibility between the techniques described to make a catheter MRI conspicuous and X-ray conspicuous. Thus, any catheter or similar device, using the technology delineated herein, may be rendered easily detected on both MRI scans and X-ray scans without degradation of either type of image.

BRIEF SUMMARY OF THE INVENTION

In general it is an object of the present invention to provide a device construction and method which will facilitate visibility of the device when inserted into a body being subjected to magnetic resonance imaging.

Another object of the invention is to provide a device construction and method of the above character in which the device is caused to exhibit a characteristic under magnetic resonance imaging which differs substantially from that of the body in which it is positioned so that the visibility of the device under magnetic resonance imaging with respect to the surrounding body tissue is substantially enhanced.

Another object of the invention is to provide a device construction and method of the above character in which the device is made to appear slightly larger than it is when imaged to facilitate detection.

Another object of the invention is to provide a device construction and method of the above character which will cause the device to appear as a void with or without adjacent bright bands on the magnetic resonance image contrasting with the surrounding body tissues.

Another object of the invention is to provide a device construction and method of the above character in which increased contrast is provided with respect to the surrounding environment.

Another object of the invention is to provide a device construction and method of the above character in which the device has incorporated therein substances having significantly different proton density, T1, and T2 values with respect to the surrounding body tissue.

Another object of the invention is to provide a device construction and method of the above character in which embedded ferromagnetic magnetic particles are utilized.

Another object of the invention is to provide a device construction and method of the above character in which paramagnetic substances are utilized.

Another object of the invention is to provide a device construction and method of the above character in which the magnetic resonance detection capability provided does not preclude x-ray and CT detection.

Another object of the invention is to provide a device construction and method of the above character in which the device can be readily detected using magnetic resonance and x-ray imaging.

Additional objects and features of the invention will appear from the following description in which the preferred embodiments are set forth in detail in conjunction with the following drawings.

BRIEF DESCRIPTION OF THE DRAWINGS

FIG. 1 is a side elevational view of a general purpose catheter incorporating the present invention.

FIG. 2 is an enlarged cross-sectional view taken along the line 2—2 of FIG. 1.

FIG. 3 is a side elevational view of a naso-gastric tube incorporating the present invention.

FIG. 4 is an enlarged cross-sectional view taken along the line 4—4 of FIG. 3.

FIG. 5 is a side elevational view of a Foley catheter incorporating the present invention.

FIG. 6 is an enlarged cross-sectional view taken along the line 6—6 of FIG. 4.

FIGS. 8 and 9 are enlarged cross-sectional views taken along the lines 8—8 and 9—9 respectively of FIG. 7.

DETAILED DESCRIPTION OF THE INVENTION

Figure 7:
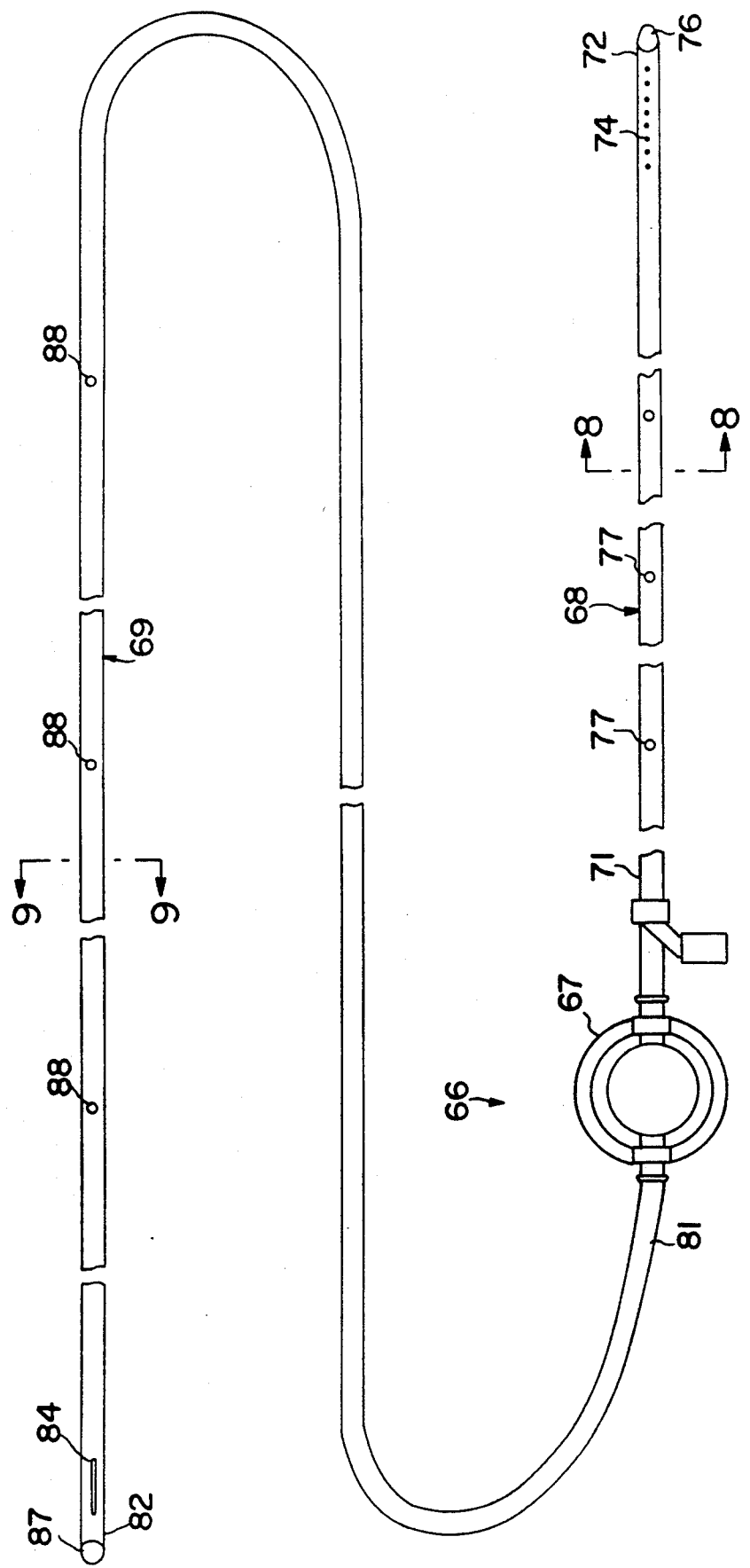
FIG. 7 is a side elevational view of a ventriculoperitoneal shunt.

In general, the device construction facilitating visibility of the device when inserted into a body being subjected to magnetic resonance imaging is comprised of a flexible tubular member formed of a material other than metal and which is adapted to be inserted into the body. Means is carried by the member exhibiting a characteristic under magnetic resonance imaging which differs substantially from that of the body in which the tubular member is positioned so that the visibility of the member under magnetic resonance imaging is substantially enhanced. This means is comprised of principally ferromagnetic, paramagnetic, or other materials which are incorporated into the member.

The method for imaging foreign objects in a body comprises the steps of inserting the foreign object into the body and causing the foreign object to exhibit a characteristic on magnetic resonance imaging which differs from the characteristic of the surrounding body so that the visibility of the foreign object is substantially enhanced under magnetic resonance imaging.

A device construction incorporating the present invention is shown in FIG. 1 and consists of a catheter 11 which is of the general drainage type. The catheter 11 is comprised of a flexible tubular member formed of a suitable material such as plastic. A suitable plastic such as polyethylene may be utilized. The tubular member is provided with a funnel-shaped portion 12a at its proximal extremity 13 and a rounded tip portion 12b at its distal extremity 14 with the portion 12c between the funnel-shaped portion 12a and the rounded closed end tip portion 12b being of substantially constant outer diameter. The tubular member 12 is provided with a flow passage or lumen 16 extending from the proximal extremity through the funnel portion 12a through the intermediate portion 12c which opens into first and second openings 17 and 18 provided on opposite sides of the tubular member and being spaced apart near the distal extremity of the tubular member.

The catheter which is shown in FIG. 1 can be in various sizes ranging from 2 French to as large as 30 French or greater depending on the application.

In accordance with the present invention in order to make the catheter 11 visible during magnetic resonance imaging (MRI), a suitable ferromagnetic material is incorporated into the plastic as the plastic is being extruded to form the tubular member 12. The ferromagnetic materials utilized produce imaging artifacts comprising a signal void with adjacent bands of elevated or bright signal intensity on the magnetic resonance image so as to make the catheter visible with respect to the surrounding body tissues. Suitable magnetic materials include iron and iron oxides. It has been found that particles of these substances can cause such imaging artifacts in magnetic resonance images that can range from less than 1.1 to over 100 times the size of the particle. The particles can have any suitable size ranging from a size which is less than the thickness of the wall of the catheter. The ferromagnetic particles which are utilized in the plastic can be distributed in the desired portions of the flexible member. In order to make an entire catheter visible, it is desirable that the ferromagnetic particles be distributed substantially uniformly throughout the catheter. This can be readily accomplished by mixing the ferromagnetic particles into the plastic as it is being extruded. It has been found that sufficient enhancement of the magnetic resonance image of the catheter can be obtained by utilizing from less than 0.001% to greater than 10% by weight of the plastic material forming the catheter but is usually 0.01% to 2% by weight depending on the magnetic field strength, gradient field strength, and the pulse sequences used by the specific MRI system being utilized, as well as the size and clinical application of the catheter. The concentration is at the lower end of the range for larger catheters in low gradient strength/magnetic field strength MRI systems and increases as the catheter size decreases and gradient strength/magnetic field strength increases.

It should be appreciated that rather than having the ferromagnetic particles distributed uniformly throughout the catheter, it is possible to provide the ferromagnetic particles only in a portion of the catheter, as for example, the distal extremity or for example in bands extending circumferentially around the catheter and being spaced apart axially of the catheter at various regions of the catheter. Such spot locating of the ferromagnetic particles may be desirable where it is particularly important to be able to ensure that portions of the body tissue will not be excluded from the image by the imaging artifacts created by the ferromagnetic particles in the catheter.

Rather than providing the ferromagnetic particles in spot locations spaced axially of the catheter, it also may be desirable to place the magnetic particles in one or more stripes extending longitudinally of the catheter. This can be readily accomplished by introducing the ferromagnetic particles into the extruder at one circumferential region of the catheter as it is being extruded so that a stripe of the ferromagnetic particles is formed in the catheter extending the entire length of the catheter. In the utilization of a stripe it may be desirable to provide a greater concentration of the ferromagnetic particles in limiting the area and thereby limiting the extent of the imaging artifact created in the magnetic resonance image and also thereby minimizing the extent that the imaging artifact would degrade viewing of the surrounding tissue of the body into which the catheter is introduced.

Another embodiment of the invention is shown in FIGS. 3 and 4 in which a naso-gastric catheter 21 is provided. It is comprised of a flexible elongate tubular member 22 formed of a suitable material such as plastic. Various plastics can be utilized such as polyethylene. The flexible tubular member 22 is provided with proximal and distal extremities 23 and 24. The proximal extremity 23 is provided with a funnel-shaped portion 22a, a rounded closed end tip portion 22b on the distal extremity and an intermediate portion 22c which is substantially circular in cross-section and of substantially uniform diameter throughout its length. The flexible tubular member 22 can be formed in a suitable manner such as by extruding and is provided with a main lumen 26 and side moon-shaped lumens 27 and 28. The tubular member 22 is provided with a plurality of holes 29 and 31 in the region of its distal extremity which are spaced apart and are arranged in a spiral fashion around the circumference of the tubular member. Certain of the holes 29 are in communication with the main lumen 26 whereas other of the holes 31 are in communication with the side lumen 27.

Another flexible tubular member 32 is provided which has its distal extremity 33 inserted into an opening 34 provided in the funnel-shaped portion 22a of the flexible tubular member 22. The proximal extremity 36 of the tubular member 32 is funnel shaped. A flow passage (not shown) extends through the tubular member 32. This flow passage is in communication with the lumen 27 provided in the main flexible tubular member 22. An adapter 37 is provided which can be formed of a suitable material such as plastic. The adapter 37 is provided with tapered extremities on opposite ends which are adapted to fit within the funnel-shaped portions of the main flexible tubular member 22 and of the tubular member 32. The flexible tubular member 22 is provided with a white stripe 41 extending longitudinally of the flexible tubular member 22 from the proximal to the distal extremity of the same. This white stripe 41 is formed of a material which is visible to a human eye, as for example, barium to provide a white stripe. The white stripe can be formed in a suitable manner such as by introducing barium into the extruder as the tubing is being extruded for forming the flexible tubular member 22. A plurality of spaced apart markers 42 are provided on the flexible member 22 and are spaced apart rearwardly from the holes 29 and 31 and can be formed of a suitable material such as a black pigment which is impregnated into the plastic forming the tubular member 22. These markers 42 are provided so that there is an indication of the depth to which the catheter has been inserted into the body.

Means is carried by the flexible elongate tubular member 22 which exhibits a characteristic under magnetic resonance imaging which differs substantially from that of the body so that the visibility of the flexible tubular member under magnetic resonance imaging is substantially enhanced. This means takes the form of a liquid or gel contrast agent which can be introduced into the lumen 28. The liquid contrast agent can be introduced into the lumen 28 through a flexible tubular member 46 which is mounted in the funnel-shaped portion 22a much in the same manner as the flexible tubular member 32.

The flexible elongate member 46 is provided with a lumen (not shown) which is in communication with the lumen 28 and which is connected to a Luer-type fitting 47 carried by the flexible member 46. The contrast agent can then be introduced through the fitting 47 to fill the lumen 28 so that the contrast agent extends through the entire length of the catheter. In the event there is difficulty in filling the lumen because of entrapped air in the lumen 28, a flexible vent tube can be provided to vent the lumen and the lumen can be filled while the catheter is outside the body. If desired, the vent tube can thereafter be removed before insertion of the catheter into the body. Similarly, if desired, self-vent means can be provided for the catheter of a type well known to those skilled in the art.

By way of example, the contrast agent can be a paramagnetic agent which is significantly different T1 and T2 values from the surrounding tissue. The substances having the tailored T1 and T2 characteristics can be included in aqueous solutions or suspensions. These paramagnetic substances can be transition metal ions such as gadolinium, chromium, nickel, copper, iron and manganese. The concentration of the paramagnetic agent in the solution of liquid can range from the micromolar to the millimolar concentrations. It should be appreciated that other agents exhibiting paramagnetic characteristics such as stable free radicals including nitroxyls can be utilized in a similar manner. The contrast agent may also be mineral oil.

It also should be appreciated that non-paramagnetic substances having desirable relaxation times also can be utilized and can be placed within a separate lumen within the catheter or other similar device to make the device detectable by magnetic resonance imaging. By way of example, mineral oil is a substance which can fulfill such requirements.

When a device made in accordance with the present invention is inserted into the body utilizing a contrast agent, dependent upon the particular contrast agent used, the device will appear either relatively bright or relatively dark in comparison with the surrounding body structure when viewed in magnetic resonance imaging.

It should be appreciated that if desired in place of the separate lumen 28, the catheter which is shown in FIGS. 3 and 4 and be constructed so that it carries means exhibiting a characteristic under magnetic resonance imaging which differs substantially from that of the body using the ferromagnetic agents specified in connection with the catheters shown in FIG. 1 in which the agent can be incorporated into the plastic material from which the device is made. The visibility of the device is thereby substantially enhanced.

Another embodiment of the invention is shown in FIGS. 5 and 6 in which a Foley catheter 51 is shown. The Foley catheter is comprised of a flexible elongate tubular member 52 formed of a suitable material such as a latex material. The tubular member is provided with proximal and distal ends 53 and 54. The proximal end of the tubular member 52 is provided with a funnel-shaped portion 52a whereas the distal portion is provided with a rounded tip 52b and an intermediate portion 52c of circular cross-section which is substantially uniform throughout its entire length. First and second lumens 56 and 57 are provided in the tubular member 52. The large lumen 56 extends through the large funnel portion 52a and opens through a pair of holes 58 provided in the distal extremity of the tubular member 52. The second lumen 57 is in communication with a lumen (not shown) in a side arm 59 that has a one-way valve 61 carried thereby. The second lumen 57 terminates in a balloon (not shown) provided internally near the distal extremity of the tubular member 52. The balloon is adapted to be inflated by suitable means such as by introduction of a saline solution once the catheter is in place in the bladder to prevent the catheter from falling out of the bladder.

Means is also carried by the catheter 51 which exhibits a characteristic under magnetic resonance imaging which differs substantially from that of the body in which the catheter is placed so that the visibility of the catheter under magnetic resonance imaging is substantially enhanced. This can be accomplished by the construction and method disclosed in FIG. 1 or, alternatively, in FIG. 2. However, in this case, the separate lumen 57 provided for inflating the balloon can be utilized for carrying the liquid contrast agent which provides contrast with surrounding tissues under magnetic resonance imaging. Thus a liquid of the type hereinbefore described carrying paramagnetic substances can be utilized for inflating and deflating the balloon and thus accomplish two functions at the same time, namely, inflating and deflating the balloon and the other making the catheter more visible under magnetic resonance imaging. Alternatively, as hereinbefore described, ferromagnetic materials can be incorporated into the materials which make up the flexible tubular member 52.

Similarly, balloon angioplasty catheters and like devices may also be designed so that they may be detected on MRI scans. The catheter material may be impregnated with ferromagnetic material and/or the balloon or other lumen may be filled with a material that would render the catheter and balloon conspicuous on MRI scans.

In FIGS. 7, 8 and 9, another embodiment of the invention is shown in the form of a ventriculo-peritoneal shunt tube 66. Such a tube is typically used for draining excess cerebrospinal fluid that collects inside the ventricles within the brain and drains this fluid into the peritoneum. The shunt tube 66 consists of a plastic one-way valve assembly 67 to which are connected a first tubular member 68 and a second tubular member 69. The first tubular member 68 has its proximal extremity 71 mounted on the valve assembly 67 and has a distal extremity 72 which is rounded as shown. The first tubular member 68 is provided with a lumen 73 extending therethrough which is in communication with the valve member 67 and which is in communication with a plurality of holes 74 arranged in rows extending axially of the tubular member 68 and being spaced in circumferential rows around the tubular member 68 as, for example, in four rows spaced 90°. A radiopaque marker 76 is provided on the distal extremity 72 and is formed of a suitable material such as gold. Additional markers 77 are provided on the tubular member 68 and as shown can take the form of circular dots which are visible to the human eye and formed of a suitable material such as a black pigment.

The second elongate flexible member 69 is provided with proximal and distal extremities 81 and 82. The proximal extremity is secured to the valve assembly 67. The distal extremity is rounded as shown. The flexible elongate member 69 is provided with a lumen 83 which extends therethrough from the valve assembly 67 to a plurality of slits 84 extending longitudinally of the flexible elongate member 69 and spaced circumferentially around the flexible elongate member 69 such as for example, for providing four of such slits spaced 90° apart. A radiopaque marker 87 is carried by the distal extremity 82 and is formed of a suitable material such as gold. Additional markers 88 are provided along the length of the flexible elongate member 69 and can take the form of dots of a black pigment impregnated into the material forming the flexible elongate member 69.

Means is also carried by the shunt tube 66 shown in FIGS. 7, 8 and 9 which exhibits a characteristic under magnetic resonance imaging which differs substantially from that of the body so that the visibility of the flexible tubular members under magnetic resonance imaging is substantially enhanced. Since the flexible tubular members 68 and 69 forming a part of the shunt tube 66 are relatively small in diameter, it is preferable to utilize a ferromagnetic material which can be incorporated as a part of the flexible tubular members and thereby not appreciably affect the size of the tubular members. However, if desired, an additional lumen can be provided within each of the flexible tubular members. However, this normally would be undesirable because it would make it necessary to enlarge the diameter of the flexible tubular member. If an additional lumen is utilized, a contrast agent can be introduced into the lumen in a manner similar to that hereinbefore described with the previous embodiments.

From the foregoing it can be seen that a device construction and method have been provided which makes it possible to substantially enhance the visibility of the device which is a foreign object in the body. This makes it possible to visualize the placement of the device using magnetic resonance imaging and thereafter to ascertain the location of the device to ascertain whether or not it has moved or whether or not it is in the proper position in the body. The methods and constructions herein disclosed utilizing ferromagnetic particles can be particularly useful for labeling ventriculo-peritoneal shunts, nasogastric tubes, feeding tubes, urinary catheters, intravascular angioplasty catheters, other drainage catheters and other devices which reside in regions which may appear either bright or dark on magnetic resonance scans.

The paramagnetic agents or other contrast agents can be utilized for labeling catheters and other devices which would appear either relatively bright or dark in comparison with the surrounding body structure. Such devices typically would be nasogastric, feeding, urinary, rectal, endotracheal as well as miscellaneous drainage tubes. In addition, intravascular catheters including triple lumen, Swan-Ganz, and angioplasty catheters can also be marked for imaging on magnetic resonance imaging scans.

It should be appreciated that if desired, the material or substance which is carried by the elongate member in addition to being more visible under magnetic resonance also can be formed of a material which is relatively radiopaque so it also can be observed under x-rays if desired.

There is no intrinsic incompatibility between the techniques hereinbefore described in making a device conspicuous under MRI and also being conspicuous under x-ray imaging. Detection of devices utilizing MRI scans and X-ray scans without degradation of either type of image can be achieved. X-ray opaque materials can be impregnated into the device material, either diffusely or in specific localized areas in the form of stripes, bands, etc. X-ray opaque materials are disclosed in the prior art and can take the form of radiopaque resins, or other similar compositions such as disclosed in U.S. Pat. Nos. 3,645,955, 4,282,976, 4,581,390 and 3,749,134 or barium, bismuth or similar radiodense salts as in U.S. Pat. No. 3,529,633, 3,608,555 and 2,857,915. Similarly, x-ray opaque markers such as metal markers may be placed in the specific desired locations on a device for a variety of purposes including marking the position of the device in its entirety or marking the specific functional elements of the device such as ports, lumens, balloons, etc. Such markers may be formed of any suitable x-ray opaque metal such as platinum, such as in U.S. Pat. Nos. 4,323,071 and 4,448,195.

In connection with making devices visible under x-ray and still retaining their visibility under MRI, non-ferrous materials may be used as x-ray markers. However, in order to preclude degradation of both magnetic resonance and X-ray (computed tomographic) images, it is important that such markers be small to minimize the artifacts that may be generated. Non-ferrous metals such as gold will not as seriously degrade the magnetic resonance image and thus may be larger if it is necessary for clinical purposes to assure detection or marking on conventional or CT x-ray images.

If there is chemical incompatibility between the materials utilized to produce the x-ray and magnetic resonance image conspicuity, such materials may be physically separated in the device. Examples for such procedures can include the following. The device may be diffusely impregnated with a ferro-magnetic agent to obtain MRI conspicuity except for a longitudinal stripe which will contain the material necessary for x-ray detectability. Alternatively, in place of the longitudinal strip for x-ray detectability, the x-ray opaque material may be placed in circumferential bands or other shapes spaced longitudinally of the device. Alternatively, the materials for obtaining the two different types of conspicuity may be interchanged in their positions in the device. In another configuration, the two types of materials for MRI and x-ray conspicuity may be placed in two longitudinal strips with one stripe carrying one material and the other stripe carrying the other material. These stripes may be spaced apart or may be contiguous along the circumference of the device.

From the foregoing it can be seen that any catheter or other implantable device may be made conspicuous on MRI scans and also be at least partially conspicuous with conventional x-ray and CT scans. In general the first approach is one in which the material used to provide the conspicuity, i.e., a ferromagnetic material is incorporated into the catheter or device. The material can be distributed uniformly throughout the catheter or device or may be placed in specific clincially desirable locations within the catheter or device. The concentration or amount of ferromagnetic material in a specific catheter depends upon the type of ferromagnetic material, the size, type and clinical function of the catheter or device and the magnetic field strength, gradient strength and pulse sequences used by the MRI apparatus in which the catheter or device is to be scanned. Catheters which are manufactured in this manner will produce both very bright and very dark stripes and/or bands and will be conspicuous when passing the catheter or device through bright, dark and intermediate signal intensity and anatomic regions on MRI scans. The incorporation of a ferromagnetic material into the catheter or device is particularly desirable for catheters or devices which are very small in size because their apparent size on MRI can be adjusted by utilizing more ferromagnetic material to give an image of the catheter which is greater than the minimum spatial resolution of the MRI apparatus being used.

The second approach which has been utilized is the placement of an appropriate liquid or gel or similar material into a preexisting lumen (which does not communicate into the patient, e.g., a Foley catheter balloon lumen) or into a specially created additional lumen (e.g. the hereinbefore described nasogastric tube). The liquid or gel must be tailored so that its proton density, T1 and T2 (or other MRI characteristic) are appropriate for the clinical environment and the MRI apparatus in which scanning is to take place. If an additional lumen is added to a preexisting catheter or device, this lumen may be of any particular geometry either running the length or surrounding or encircling the catheter or placed in one or more segments of the body of the catheter. If the catheter must be seen in a variety of clinical environments, additional lumens filled with substance of different proton density (T1 and T2 or other MRI characteristic) may be added to improve MRI conspicuity in these different regions. Catheters which are manufactured in this manner will be conspicuous from the material contained within the lumen or lumens as having different MRI characteristics than the surrounding body tissue.

It should be appreciated in connection with the present invention that the devices may carry a single material to make the device conspicuous under MRI that exhibit sufficient x-ray opacity to make the device visible under high quality x-ray images and particularly high resolution CT scans. Such a result may be achieved with a device impregnated with a ferromagnetic agent.

What is claimed is:

1. A catheter which is specifically useful during a magnetic resonance imaging of body tissue comprising:
    a contrast agent;
    a flexible tubular member having a first lumen with an additional lumen positioned therein, the additional lumen retaining the contrast agent therein;
    the flexible tubular member being made of resinous material and adapted to be inserted in the body tissue, the flexible tubular member having ferromagnetic particles embedded therein at a concentration of about 0.001% to about 10% by weight of the material wherein, under magnetic resonance imaging, the flexible member exhibits characteristics which differ substantially from characteristics of the body tissue so that the visibility of the flexible member under magnetic resonance is substantially enhanced, resulting in the flexible member being distinguishable from adjacent tissue as a dark area in brighter tissues and as a bright area in darker tissues, said member being free of elements which tend to degrade the overall quality of magnetic images of the body tissue.

2. The catheter of claim 1, wherein the contrast agent is a liquid having a paramagnetic substance therein.

3. The catheter of claim 2, wherein the paramagnetic substance is selected from the group consisting of transition metal ions including gadolinium, nickel, chromium, copper, iron and manganese.

4. The catheter of claim 2, wherein the paramagnetic substance is selected from the group consisting of stable-free radicals including nitroxyls.

5. The catheter of claim 2, wherein the contrast agent is a mineral oil.

6. The catheter of claim 1, wherein the contrast agent exhibits substantially different proton density and T1 and T2 values from the surrounding tissue in the body tissue in which it is positioned.

7. The catheter of claim 1, wherein the contrast agent is of a substantially different magnetic suspectability and has substantially different diffusion and motion characteristics from the surrounding tissue of the body tissue in which the catheter is placed.

8. The catheter of claim 1, wherein at least one of the lumens is a balloon lumen.

9. A catheter which is specifically useful during magnetic resonance imaging of body tissue comprising:
a contrast agent;
a flexible tubular member having a first lumen with an additional lumen positioned therein, the additional lumen retaining the liquid contrast agent.

10. The catheter of claim 9, wherein the contrast agent is a liquid having a paramagnetic substance therein.

11. The catheter of claim 9, wherein the contrast agent exhibits substantially different proton density and $T_1$ and $T_2$ values from the surrounding tissue in the body tissue in which the catheter is positioned.

12. The catheter of claim 9, wherein the contrast agent is a mineral oil.

13. A catheter which is specifically useful during magnetic resonance imaging of body tissue, while being X-ray/CT detectible and compatible, comprising:
a contrast agent;
a flexible tubular member having a first lumen with an additional lumen positioned therein, the additional lumen retaining the contrast agent;
the flexible tubular member being made of resinous material and adapted to be inserted in the body tissue, the flexible tubular member having ferromagnetic particles embedded therein at a concentration of about 0.001% to about 10% by weight of the material wherein, under magnetic resonance imaging, the flexible member exhibits characteristics which differ substantially from characteristics of the body tissue so that the visibility of the flexible member under magnetic resonance is substantially enhanced, resulting in the flexible member being distinguishable from adjacent tissue as a dark area in brighter tissues and as a bright area in darker tissues, said member being free of elements which tend to degrade the overall quality of magnetic images of the body tissue.

14. The catheter of claim 13, wherein at least one of the lumens is a balloon lumen.

* * * * *